`US005500087A`

United States Patent [19]
Bernard et al.

[11] Patent Number: 5,500,087
[45] Date of Patent: Mar. 19, 1996

[54] PAPER PRODUCTS USING STARCHES MODIFIED WITH AMINO-MULTICARBOXYLATES

[75] Inventors: Karen A. Bernard, Gaithersburg, Md.; John Tsai, Belle Mead, N.J.; Robert L. Billmers, Stockton, N.J.; Robert W. Sweger, Bound Brook, N.J.

[73] Assignee: National Starch and Chemical Investment Holding Corporation, Wilmington, Del.

[21] Appl. No.: 447,462

[22] Filed: May 23, 1995

Related U.S. Application Data

[62] Division of Ser. No. 190,824, Feb. 2, 1994, Pat. No. 5,455,340.

[51] Int. Cl.$^6$ .......................... D21H 13/00; D21H 15/00
[52] U.S. Cl. ........................ 162/164.6; 162/175
[58] Field of Search ................... 162/164.6, 175

[56] References Cited

U.S. PATENT DOCUMENTS

| | | | |
|---|---|---|---|
| 3,459,632 | 8/1969 | Caldwell et al. | 162/175 |
| 3,751,422 | 8/1973 | Bowden | 546/260 |
| 3,880,832 | 4/1975 | Tessler | 536/50 |
| 4,017,460 | 4/1977 | Tessler | 536/50 |
| 4,119,487 | 10/1978 | Tessler | 162/175 |
| 4,260,738 | 4/1981 | Tessler | 536/49 |
| 4,705,889 | 10/1987 | Hendricks et al. | 562/564 |

FOREIGN PATENT DOCUMENTS 590176  1/1960  Canada.

OTHER PUBLICATIONS

R. L. Whistler et al., *Starch: Chemistry and Technology*, Second Edition, 1984, pp. 332–364.
D. R. Howton, *J. Amer. Chem. Soc.*, "1,3–Dimethylpiperidone–4", 1945, pp. 277–282.
S. I. Suminov et al., *Russian Chem. Rev.*, "Nucleophilic Addition of iAmino–groups to an Activated Carbon–Carbon Double Bond", 38(11), 1969, pp. 884–899.

*Primary Examiner*—Nathan M. Nutter
*Attorney, Agent, or Firm*—Eugene Zagarella, Jr.

[57] ABSTRACT

Amino-multicarboxylate starch ether derivatives are provided having the following structure:

$$St-O+CH_2\rightarrow_n N \begin{matrix} R' & R \\ | & | \\ CH-CH-COOM \\ \\ CH-CH-COOM \\ | & | \\ R' & R \end{matrix} \quad \text{or}$$

$$St-O+CH_2\rightarrow_n N \begin{matrix} COOM & R \\ | & | \\ CH-CH-COOM \\ \\ R'' \end{matrix}$$

wherein
  St-O represents a starch molecule,
  R is H or $CH_3$;
  R' is H, $CH_3$ or COOH;
  M is a cation;
  n is 2 or 3; and
  R" is H or alkyl of 1 to 18 carbon atoms.

These starch derivatives are particularly useful as retention and strength aids in papermaking.

13 Claims, No Drawings

PAPER PRODUCTS USING STARCHES MODIFIED WITH AMINO-MULTICARBOXYLATES

This application is a division of application Ser. No. 08/190,824, filed Feb. 2, 1994, and now U.S. Pat. No. 5,455,

BACKGROUND OF THE INVENTION

This invention relates to novel modified starches and particularly amino-multicarboxylate starch derivatives and reagents used in the preparation thereof.

The modification of starch by chemical derivatization and, in particular, the preparation of starch ethers and esters is well known in the art. The addition of cationic or anionic substituent groups to form cationic or anionic starch derivatives is also well known. A discussion of the preparation of cationic or anionic starch derivatives may be found in "Starch: Chemistry and Technology", Second Edition, edited by R. L. Whistler, et al., 1984, pp. 332–364.

It is further known to add both cationic and anionic substituent groups to starch to form amphoteric starch ether derivatives. Typical prior art methods involve either an "in situ" formation of the amphoteric starch ether derivatives by simultaneous reaction of two different chemical modifying agents with the starch as described in U.S. Pat. Nos. 3,459,632 and 4,119,487 or a multi-step procedure where the chemical modifications of the starch are carried out in sequence as described in U.S. Pat. No. 3,751,422.

It is also known to add mono-cationic and mono-anionic substituent groups to the same reactive site in the starch molecule, thereby forming zwitterion starch ether derivatives. The preparation of a zwitterion starch ether derivative, wherein the zwitterion substituent groups are amino-monocarboxylic acid groups, is described in U.S. Pat. No. 4,017,460. In this patent the derivatives are prepared by reacting the starch base with a reagent obtained by reacting a secondary amine with a dihalopropionic acid or alkyl ester thereof. The resulting zwitterion group contains one anionic carboxyl group bound directly to a cationic amine group. Another zwitterion starch ether derivative is disclosed in U.S. Pat. No. 4,260,738 where the zwitterion substituent groups are aminophosphonic acids or their salts.

In contrast to the amino-monocarboxylic acid zwitterion starch ethers described in the aforementioned U.S. Pat. No. 4,017,460, the novel starch derivatives of this invention contain amino-multicarboxylate groups as the amphoteric or zwitterion substituent group. These amino-multicarboxylate starch derivatives possess different charge ratios and exhibit properties making them especially useful in papermaking as retention and strength aids and as metal chelating agents.

SUMMARY OF THE INVENTION

In accordance with this invention, zwitterion starch derivatives with multicarboxylate groups are provided having the following structure:

$$St-O-(CH_2)_n-N\begin{pmatrix} CH-CH-COOM \\ | \quad | \\ R' \quad R \\ \\ CH-CH-COOM \\ | \quad | \\ R' \quad R \end{pmatrix} \quad (I)$$

or $$St-O-(CH_2)_n-N\begin{pmatrix} COOM \quad R \\ | \quad / \\ CH-CH-COOM \\ \\ R'' \end{pmatrix} \quad (Ia)$$

wherein

St-O represents a starch molecule or a modified starch molecule (wherein the hydrogen of a hydroxyl group of an anhydroglucose unit has been replaced as shown);

R is H or $CH_3$;

R' is H, $CH_3$ or COOH;

M is a cation, more particularly H, alkali metal, alkaline earth metal or ammonium;

n is 2 or 3; and

R" is H or alkyl of 1 to 18 carbon atoms.

The starch derivatives (I) and (Ia) were prepared by reacting starch with selective amino-multicarboxylic acid reagents having the following formula:

$$X(CH_2)_n-N\begin{pmatrix} CH-CH-COOH \\ | \quad | \\ R' \quad R \\ \\ CH-CH-COOH \\ | \quad | \\ R' \quad R \end{pmatrix} \cdot HX \quad (II)$$

or $$X(CH_2)_n-N\begin{pmatrix} COOH \quad R \\ | \quad / \\ CH-CH-COOH \\ \\ R'' \end{pmatrix} \cdot HX \quad (IIa)$$

where X is halogen;

R is H or $CH_3$;

R' is H, $CH_3$ or COOH;

N is 2 or 3; and

R" is H or alkyl of 1 to 18 carbon atoms.

The reagents (II) and (IIa) were provided by the reaction of selected esters such as alkyl acrylates with aminoalcohols followed by halogenation such as chlorination with thionyl chloride and hydrolysis.

DETAILED DESCRIPTION OF THE INVENTION

In preparing the starch ether derivatives of this invention it is first necessary to provide selected multicarboxylate reagents (II) or (IIa). These reagents are prepared by a Michael reaction between an aminoalcohol and a selected ester containing an activated olefin followed by halogenation with any halide and more particularly chlorination or bromination with chlorination being preferred. The chlorination may be carried out using chloride compounds such as thionyl chloride or phosphorus oxychloride. Purification such as by steam stripping or recrystallization from isopropanol or other suitable solvents may be employed, if desired, to improve the purity of the reagent and increase the efficiency of the subsequent starch reaction.

The above noted reaction scheme in preparing the reagent (II) is illustrated below where ethanolamine is reacted with methyl acrylate followed by chlorination with thionyl chloride and hydrolysis to provide the aminodicarboxyl containing reagent, 2-chloroethylaminodipropionic acid:

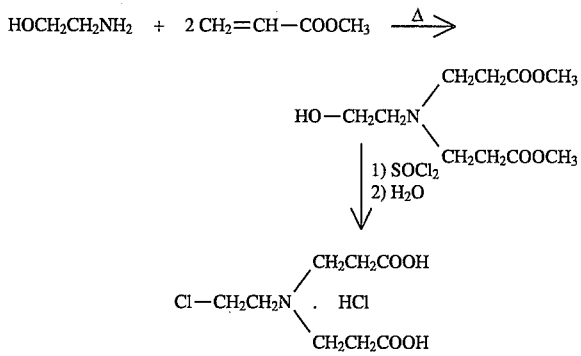

The aminoalcohol used in preparing the multicarboxylic acid reagent (II) or (IIa) will generally have the formula

where R is H or alkyl of 1 to 18, preferably 1 to 8 carbon atoms, n is 2 or 3, and the olefin containing ester will be any such ester, for example, alkyl acrylates, alkyl methacrylates or alkyl crotonates and more particularly will have the formula:

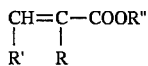

where R is H or CH$_3$, R' is H or CH$_3$ and R" is alkyl, and more particular, methyl, ethyl or propyl. Diesters of olefin containing esters, e.g., dialkyl maleates may be used to prepare the multicarboxylic acid reagents, particularly when the noted aminoalcohol has an alkyl R group.

The formation of the zwitterion starch derivative (I) or (Ia) involves reacting the selected multicarboxylate reagent (II) or (IIa) with a starch base in an aqueous medium using either an aqueous slurry or an aqueous dispersion of the starch base. The reaction is carried out under alkaline conditions at a pH of from about 9.5 to 13, more particularly from about 11 to 12.5 and preferably from about 11.4 to 12.4. The pH is conveniently controlled by the periodic addition of a dilute aqueous solution of sodium hydroxide or other common base including potassium hydroxide, calcium hydroxide, sodium carbonate, ammonium hydroxide, tetramethylammonium hydroxide, etc. The preferred bases are sodium and calcium hydroxide.

The reaction is carried out at a temperature of from about 10° to 95° C., preferably from about 20° to 50° C. It will be recognized that the use of temperatures above about 60° C. with granular starches in an aqueous medium will result in granule swelling and filtration difficulties or gelatinization of the starch.

When conducting the reaction with granular starches, it may sometimes be desirable to carry out the reaction in the presence of salts, e.g., sodium sulfate, in amounts of from about 10 to 40% by weight, based on dry starch. The presence of sodium sulfate acts to suppress swelling of the starch and gives a more filterable product. The sodium sulfate does not have to be used in the calcium hydroxide reactions The amount of zwitterion multicarboxylate reagent (II) or (IIa) to be employed in the reaction will vary from about 0.1 to 100% by weight, based on the weight of dry starch, and depending on such factors as the starch base used, the particular multicarboxylate reagent used, the degree of substitution required in the end product, and to some extent, the reaction conditions used. In general, the preferred amount of reagent to be used when preparing the zwitterion starch ether derivative containing amino-multicarboxylate groups is about 0.3 to 10% by weight for granular starches and about 15 to 75% by weight for non-granular starches.

The multicarboxylate reagent may be added to the reaction mixture as a solid or an aqueous solution. The preferred concentration of the solution is 20 to 50% by weight, based on the weight of the reagent. In an alternative method, the carboxylate reagent solution is brought to the desired alkaline pH prior to its addition to the starch base. In this alternative method, the reagent is in the form of a salt rather than an acid or partially neutralized acid when it is introduced to the reaction mixture. In another variation dry starch may be added to an alkaline solution of the carboxylate.

Reaction time will vary from about 0.2 to 24 hours depending on such factors as the amount, stability and reactivity of the multicarboxylate reagent employed, the temperature, pH, the scale of reaction and the degree of substitution desired. In general, the preferred range of reaction time is from about 1 to 16 hours.

After completion of the reaction, the pH of the reaction mixture is adjusted to from about 3 to 9 with any commercial acid such as hydrochloric acid, sulfuric acid, acetic acid, etc. Such acids may be conventionally added as a dilute aqueous solution. Depending on the final pH and the base used, the carboxyl group can be present as either the carboxylic acid or the corresponding salt. The cation M as found in starch derivatives (I) and (Ia) can be any cation and more particularly, hydrogen, an alkali metal, an alkaline earth metal or ammonium. In the case of a multi-valent cation, e.g., calcium, the structure of the derivative could be cyclic.

Recovery of the resulting starch ether derivatives may be readily accomplished, with the particular method employed being dependent on the form of the starch base. Thus, a granular starch is recovered by filtration, optionally washed with water to remove any residual salts, and dried. The granular starch products may also be drum-dried, spray-dried, or gelatinized and isolated by alcohol precipitation or freeze drying to form non-granular products (i.e., gelatinized). If the starch product is non-granular, it may be purified by dialysis to remove residual salts and isolated by alcohol precipitation, freeze drying, or spray drying.

The applicable starch bases which may be used in preparing the starch ether derivatives herein may be derived from any plant source including corn, potato, sweet potato, wheat, rice, sago, tapioca, waxy maize, sorghum, high amylose corn, or the like. Also included are the conversion products derived from any of the latter bases including, for example, dextrins, prepared by the hydrolysis of acid and/or heat; oxidized starches prepared by treatment with oxidants such as sodium hypochlorite; fluidity or thin-boiling starches prepared by enzyme conversion or mild acid hydrolysis; and derivatized starches such as ethers and esters. Starch esters will undergo hydrolysis when exposed to reaction conditions needed to prepare starch ethers. If mixed starch ethers/esters are desired, it is obvious to those skilled in the art that the ether substituents must be reacted first, followed by esterification. The intermediate starch ether can be directly esterified or isolated and purified prior to esterification. The starch base may be a granular starch or a gelatinized starch, i.e., non-granular starch.

The preferred starch derivatives (I) and (Ia) of this invention as described above, are those wherein R, R', and R" are hydrogen, M is hydrogen and n is 2 and more particularly those having the structure (I). Also the starch base and the resulting starch derivatives may be further derivatized or modified with other groups such as cationic groups which are known and used in the paper industry. Particularly useful cationic starches are the tertiary aminoalkyl starch ethers such as 2-diethylaminoethyl chloride and quaternaryammonium starch ethers such as 2,3-epoxypropltrimethylammonium chloride.

The novel starch ether derivatives of this invention may be used as wet end additives in papermaking and particularly are useful in providing strength and pigment retention properties. The term "paper," as used herein, includes sheet-like masses and molded products made from fibrous cellulosic material, which may be derived from natural sources, synthetics such as polyamides, polyesters, rayon and polyacrylic resins as well as from mineral fibers such as asbestos and glass. In addition, paper made from combinations of cellulosic and synthetic materials are applicable herein. Paperboard is also included within the broad term "paper".

Papermaking, as it is conventionally known, is a process of introducing an aqueous slurry of pulp or wood cellulosic fibers (which have been beaten or refined to achieve a level of fiber hydration and to which a variety of functional additives can be added) onto a screen or similar device in such a manner that the water is removed, thereby forming a sheet of the consolidated fibers, which upon pressing and drying can be processed into dry roll or sheet form. Two well known papermaking operations involve the Fourdrinier machine, the most common, and the cylinder machine. In the Fourdrinier and multicylinder operations, and in other machine operations, as typical in papermaking, the feed or inlet to the machine is an aqueous slurry or water suspension of pulp fibers which is provided from what is called the "wet end" system. In the wet end, the pulp along with other additives are mixed in an aqueous slurry and subject to mechanical and other operations such as beating and refining to improve interfiber bonding and other physical properties of the finished sheet. Additives commonly introduced along with the pulp fibers are pigments such as titanium dioxide, mineral fillers such as clay and calcium carbonate and other materials introduced into paper to achieve such properties as improved brightness, opacity, smoothness, ink receptivity, fire retardance, water resistance, increased bulk, etc.

The practitioner will recognize that the structure of the zwitterion starch derivatives will vary depending upon the pH of the solution and upon the cations present in the paper pulp. Therefore, the exact structure of the modified starch in the paper pulp may be complex and it may contain the same or different cations and one or more different cations depending upon the valence of the cations present.

The starch derivatives described herein are used in their dispersed (i.e., cooked) form mainly as beater additives, although their addition to the pulp may occur at any point in the paper-making process prior to the ultimate conversion of the wet pulp into a dry web or sheet. Thus, for example, they may be added to the pulp while the latter is in the headbox, beater, hydropulper or stock chest.

The starch derivatives (I) used as pigment retention aids and otherwise in papermaking may be effectively used for addition to pulp prepared from any types of cellulosic fibers, synthetic fibers, or combinations thereof. Among the cellulosic materials which may be used are bleached and unbleached sulfate (kraft), bleached and unbleached sulfite, bleached and unbleached soda, neutral sulfite, semi-chemical chemi-ground wood, ground wood or any combination of these fibers. Fibers of the viscous rayon or regenerated cellulose type may also be used if desired.

Any desired inert mineral fillers may be added to the pulp which is to be modified with the starch derivatives herein. Such materials include clay, titanium dioxide, talc, calcium carbonate, calcium sulfate and diatomaceous earths. Rosin or synthetic internal size may also be present, if desired.

The proportion of the starch derivative to be incorporated into the paper pulp may vary in accordance with the particular pulp involved. In general, it is preferred to use about 0.01 to 5% and preferably about 0.05 to 2% of the starch ether derivative, based on the dry weight of the pulp. Within this preferred range the precise amount which is used will depend upon the type of pulp being used, the specific operating conditions, and the particular end use for which the paper is intended. The use of amounts of starch derivative greater than 2%, based on the dry weight of the pulp, is not precluded, but is ordinarily unnecessary in order to achieve the desired improvements. When added in the proper concentrations, the starch ether derivatives herein serve to increase pigment retention, improve drainage, and increase strength. They also may be used in conjunction with other additives to provide further improvement in paper properties. One particularly useful additive which may be used with the starch derivatives of this invention is Kymene® a cationic poly(aminoamide)-epichlorohydrin resin product available from Hercules, Inc. This product may generally be used with the starch derivatives of this invention in effective amounts and more particularly from about 0.01 to 10% by weight, based on the dry weight of pulp.

In addition to the selected starch derivative and other components that may be included in the alkaline papermaking system as described above, colloidal inorganic minerals may be added to the system to form an alkaline microparticle system. Such microparticle systems include colloidal silica, bentonite and anionic alum and may be incorporated into the system in amounts of at least 0.001% and more particularly from about 0.001 to 5% and preferably from about 0.01 to 1% by weight based on the weight of dry pulp. Further description of such microparticle inorganic materials may be found in U.S. Pat. No. 4,388,150 issued Jun. 14, 1983; U.S. Pat. No. 4,643,801 issued Feb. 17, 1987; U.S. Pat. No. 4,753,710 issued Jun. 28, 1988 and U.S. Pat. No. 4,913,775 issued Apr. 3, 1990; all of which are incorporated herein by reference.

The starch derivatives of this invention are also useful as complexing or chelating agents for various ions such as copper and calcium.

The following examples will further illustrate the embodiments of this invention. In these examples all parts are given by weight and all temperatures in degrees Celsius unless otherwise noted.

EXAMPLE I

This example illustrates the preparation of an amino-multicarboxylic acid reagent, i.e., 2-chloroethylaminodipropionic acid.

A 1,000 ml 3-neck round bottom flask fitted with a water cooled condenser, mechanical stirrer and addition funnel was charged with 30.0 g (0.49 mole) of ethanolamine. The flask was cooled to 10° C. and 84.6 g (0.98 mole) of methyl acrylate was charged to the addition funnel. One half of the methyl acrylate was added slowly to the reaction at such a rate as to maintain the reaction temperature at or below 10° C. Ethyl acetate was added to help solubilize the forming solid. The second half of the methyl acrylate was added slowly to the reaction, again keeping the temperature at or below 10° C. When the addition was completed the reaction was slowly warmed to room temperature and then heated to 48° C. and held for 18 hours. The resulting aminoalcohol can be isolated but was converted directly to the chloride as follows.

The addition funnel was charged with 183.4 ml (2.50 mole) of $SOCl_2$ and added to the reaction with cooling, maintaining the temperature below 20° C. When complete, the reaction was heated to 80° to 90° C. and held for 2 hours. When the reaction had been cooled to less than 30° C., approximately 75 ml of water was added to destroy any residual thionyl chloride and liberate the free acid. The water and other volatiles were removed under vacuum and the product purified by precipitation into isopropanol. The product and intermediate had the expected NMR's and chlorine analysis showed 13.57 percent organic chlorine (98.7 percent of theoretical).

EXAMPLE II

This example illustrates the procedure for the preparation of starch modified with amino-multicarboxylic acid reagents.

A constant temperature bath was preheated to 40° C. A total of 750 ml of water was added to a half gallon jar equipped with a mechanical stirrer, 200 g of sodium sulfate and 15 g of sodium hydroxide was dissolved in the solution. When the salts had completely dissolved, 500 g of waxy corn starch was added quickly with good agitation. A total of 20 g of the 2-chloroethylaminodipropionic acid reagent prepared in Example I was added to the reaction and the pH checked to verify that it was over 11.6. The reaction vessel was then placed into the bath and stirred for 24 hours. The reaction was then cooled to room temperature and the pH of the slurry adjusted to approximately 7.0 with dilute HCl. The starch was then filtered through Whatman #1 filter paper and the cake was washed three times with 750 ml of water and allowed to air dry to 15 percent moisture. Analysis of the starch for bound nitrogen showed 0.204% nitrogen (dry basis), indicating that the starch had been modified with the aminodicarboxylic acid functionality.

EXAMPLE III

This example further illustrates the preparation of an aminomulticarboxylate acid reagent, i.e., 2-chloroethylaminodipropionic acid.

A 250 ml 3-neck round bottom flask fitted with a water cooled condenser, mechanical stirrer and addition funnel was charged with 14.8 ml (0.245 mole) of ethanolamine. Ethyl acrylate (53.1 ml; 0.49 mole) was added dropwise over sixty minutes while the temperature was kept low using an ice-water bath (12° to 20° C.). After complete addition, the reaction was raised to 45° C. for 24 hours and then cooled to room temperature to yield 2-hydroxyethylaminodipropionate ethyl ester. The structure of the product was identified by C-13 NMR spectroscopy.

Toluene (70 ml; 0.66 mole) was added to a 250 ml 3-neck round bottom flask and thionyl chloride (22.3 ml; 0.31 mole) added. The 2-hydroxyethylaminodipropionate ethyl ester (prepared as noted above) was then charged to an equalizing addition funnel and added dropwise to the flask over approximately 90 minutes. The temperature was kept low during this phase by use of an ice-water bath (12° to 20° C.). After complete addition, the ice-bath was removed and the reaction stirred for 30 minutes. The temperature was then raised to 85° C. for 3 hours in a hot oil bath and the flask then cooled to room temperature. Deionized water (25 ml) was added to the flask to quench any remaining thionyl chloride. A condenser with collection flask was fitted to the flask along with an inlet for the addition of live steam. The flask was heated to approximately 80° C. and the product steam distilled for 30 to 60 minutes. The steam line was removed and the flask cooled to room temperature giving a reaction volume of approximately 200 ml. The aqueous product was then concentrated in vacuo to approximately 100 ml to remove any residual alcohol. Deionized water (~100 ml) was added in order to give an aqueous solution containing approximately 30% solids and 25% active Cl. The product structure was confirmed by C-13 NMR.

EXAMPLE IV

This example illustrates the procedure for the preparation of starch modified with amino-multicarboxylic acid reagent using the reagent of Example III, i.e., 2-chloroethylaminodipropionic acid.

Overhead stirring was used throughout this reaction. Water (150 ml) was added to a one liter beaker and heated to 45° C. with an external constant temperature bath. Sodium sulfate (30 g; 30% on starch) was dissolved in the water followed by the addition of potato starch (100 g) into the solution in portions to form a uniform slurry. A solution of 3% aqueous sodium hydroxide (25 ml) was added slowly with good agitation to minimize starch swelling. An aqueous solution of the 2-chloroethylaminodipropionic acid reagent (32 ml) prepared in Example III was added simultaneously with a 3% aqueous sodium hydroxide solution (170 ml) at addition rates that kept the level of caustic high (pH of about 11.0 to 11.5) in the reaction. The reaction was run at 42° to 45° C. for 16 hours and then neutralized with addition of 3N HCl to a pH of about 6.5 followed by stirring for 30 minutes. The starch was then filtered and washed two times with 150 ml of water and allowed to air dry. Analysis of the starch for bound nitrogen showed 0.25% N (dry basis) indicating that the starch had been modified with the aminodicarboxylic acid reagent.

EXAMPLE V

This example further illustrates the preparation of an aminomulticarboxylate acid reagent, i.e., 2-chloroethyl, N-methylaminosuccinic acid.

A 250 ml 3-neck round bottom flask fitted with a water cooled condenser, mechanical stirrer and addition funnel was charged with 64 ml (0.80 mole) of N-methylaminoethanol. Dimethyl maleate (100 ml, 0.80 mole) was added slowly over about 30 minutes with agitation. The reaction was warmed to 45° C. and stirred for 18 hours. When the reaction was complete, the product was transferred with 75 ml of toluene to a 1,000 ml 4-neck round bottom flask equipped with addition funnel, mechanical stirrer, oil bath and distillation head. The addition funnel was charged with 25.5 ml of thionyl chloride and added to the reaction slowly to keep the temperature at or below 35° C. After addition, the reaction was heated to 80° C. for 30 minutes. The toluene was steam distilled until the head temperature reached 98° to 100° C. for three minutes. The product was cooled and filtered and then analyzed and gave acceptable chlorine and NMR values, indicating the desired compound, i.e., 2-chloroethyl, N-methylaminosuccinic acid, had been prepared.

EXAMPLE VI

This example illustrates the use of amino-multicarboxylic acid starch derivatives for chelation of metal ions from aqueous solution.

A stock solution of 0.1 molar copper (II) nitrate was prepared by dissolving 18.7 g of copper nitrate monohydrate into 981.3 ml of water. A total of 10 ml of this solution was placed into a 50 ml beaker and 5 g of the modified starch derivative of Example II was added and stirred for 30 seconds. When the starch had settled, it had absorbed the blue color of the copper. When compared to the blank (unmodified waxy corn starch) a significant difference in color of the starch and supernatant was noted. This experiment suggests the ability of the amino-multicarboxylic acid containing starches to absorb metal ions such as copper from solution.

A 500 ml sample of standard pulp stock comprised of bleached hardwood kraft pulp (BHWK) and bleached softwood kraft pulp (BSWK) with 80:20 BHWK:BSWK, % by weight, (70% fiber and 30% calcium carbonate) was added to a Britt Jar and the pH adjusted 7.8 with dilute HCl. While stirring at 400 rpm, alum 5 lb/ton (0.25%) was added. After 20 seconds the stirring rate was increased to 2,000 rpm and after 10 seconds the starch derivative, 15 lb/ton (0.75%) was added and mixing continued for another 30 seconds. Silica, 3 lb/ton (0.15%) was then added and after 30 seconds the sample was dropped through the Britt Jar screen and a 100 ml sample was collected for evaluation using the test described above and compared to the standard or control cationic potato starch. The results are as follows:

| STARCH | FIRST PASS RETENTION (% CONTROL) | FIBER FINES RETENTION (% CONTROL) | CALCIUM CARBONATE RETENTION (% CONTROL) | TOTAL FINES RETENTION (% CONTROL) |
| --- | --- | --- | --- | --- |
| Control (Quat Potato Starch) | 77.8 (100) | 45.4 (100) | 28.5 (100) | 33.8 (100) |
| Modified Starch Sample | 86.5 (114) | 75.3 (166) | 55.3 (194) | 61.6 (182) |

EXAMPLE VII

This example illustrates the papermaking application of starches modified with amino-multicarboxylic acids.

Samples of amino-multicarboxylic acid starch derivatives of Example II as well as comparison waxy maize and cationic waxy maize samples were prepared for testing in accordance with Tappi T494 method 1982 ("Tensile Breaking Properties of Paper and Paperboard" using constant rate of elongation apparatus). A total of 1.0 g of the respective starch was dissolved in 99.0 g of water and the pH adjusted to 5.0 using hydrochloric acid or sodium hydroxide. The mixture was cooked in a boiling water bath for a total of 30 minutes with stirring for the first three minutes. The starch was then cooled and added to the pulp in the head box at the rate of 1.0 percent starch based on the dry weight of the paper or pulp. Tensile strengths of the final sheet was measured using a Model II Intellect Machine (Thwing-Albert Instrument Company, Philadelphia, Pa.), and the results are summarized below. These results indicate that dry strength can be improved by having the aminodicarboxylic acid groups on the starch.

| Sample | Dry Strength (g) |
| --- | --- |
| Waxy maize | 1,706 |
| Cationic waxy maize | 2,234 |
| Aminodicarboxylic acid waxy maize | 2,444 |

EXAMPLE VIII

This example illustrates the use of amino-multicarboxylic acid starch derivatives in microparticle wet end papermaking systems.

In the microparticle system, samples of cationic (quaternary; 0.3% N) potato starch and its amino-multicarboxylic acid starch derivative (2% treatment of reagent prepared in Example III) were prepared for testing for first pass retention (FPR), fiber fines retention, calcium carbonate retention and total fines retention in accordance with Dynamic Alkaline Retention Evaluation, Tappi T 26-pm 79 using a Britt Jar.

The results showed the significantly improved performances in retention when using the amino-multicarboxylate potato starch derivative in a microparticle papermaking system as compared to the same system using the control cationic (quat) potato starch.

EXAMPLE IX

This example further illustrates the papermaking application of aminomulticarboxylic acid starch derivatives in combination with Kymene-557, a cationic poly(aminoamide)-epichlorohydrin resin product known as a wet strength paper additive and available from Hercules.

Samples of the amino-multicarboxylic acid starch derivative (5 lb/ton of pulp) of Example II in combination with Kymene resin (10 lb/ton of pulp) were compared with a sample of the Kymene resin alone (10 lb/ton of pulp) and another sample of Kymene resin (10 lb/ton) in combination with carboxymethylated cellulose (CMC) (5 lb/ton of pulp). The samples were tested for dry tensile strength using the same procedure described in Example VII. As shown below, the results indicate that the use of the amino-multicarboxylate acid starch derivative in combination with Kymene gave improved dry strength.

| | Sample | Dry Tensile Strancrth (g/in) |
| --- | --- | --- |
| 1. | Aminodicarboxylic acid waxy maize + Kymene resin | 2523 |
| 2. | Kymene resin | 2313 |
| 3. | CMC + Kymene resin | 2400 |

What is claimed is:

1. In the method of making paper the improvement comprising adding, to the paper stock at any stage prior to forming a web, the starch ether derivative having the structure:

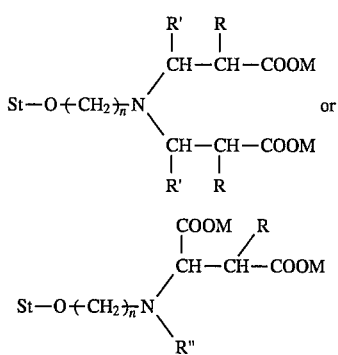

wherein

St-O represents a starch molecule,

R is H or $CH_3$;

R' is H, $CH_3$ or COOH;

M is a cation;

n is 2 or 3; and

R" is H or alkyl of 1 to 18 carbon atoms.

2. The method of claim 1 wherein in the starch ether derivative each R, R' and R" is H, and M is H.

3. The method of claim 2 wherein in the starch ether derivative n is 2.

4. The method of claim 3 wherein the starch ether derivative has the structure (I).

5. The method of claim 1 wherein from about 0.01 to 5% by weight of the starch ether derivative, based on the dry weight of pulp is used.

6. The method of claim 1 which further comprises the addition of an alkaline microparticle system containing colloidal inorganic minerals selected from the group consisting of colloidal silica, bentonite and anionic alum.

7. The method of claim 6 wherein in the starch ether derivative each R, R' and R" is H, M is H and n is 2.

8. The method of claim 7 wherein the starch ether derivative has the structure (I) and is added in an amount of from about 0.01 to 5% by weight, based on the dry weight of the pulp and from about 0.001 to 5% by weight of the colloidal inorganic mineral is added, based on the weight of dry pulp.

9. The method of claim 1 wherein a poly(aminoamide)-epichlorohydrin resin product is additionally added to the paper stock.

10. Paper made by the method of claim 1.

11. Paper made by the method of claim 4.

12. Paper made by the method of claim 6.

13. The method of claim 1 wherein the starch ether derivative M is a cation selected from the group consisting of hydrogen, alkali metal, alkaline earth metal and ammonium.

* * * * *